United States Patent
Thornton et al.

(10) Patent No.: US 11,557,392 B2
(45) Date of Patent: Jan. 17, 2023

(54) CONTEXT AND STATE AWARE TREATMENT ROOM EFFICIENCY

(71) Applicant: GYRUS ACMI, INC., Westborough, MA (US)

(72) Inventors: Thomas Michael Thornton, Harvard, MA (US); Peter Renzi, Acton, MA (US); Eddie E. Mitchell, Harvard, MA (US)

(73) Assignee: Gyrus ACMI, Inc., Westborough, MA (US)

(*) Notice: Subject to any disclaimer, the term of this patent is extended or adjusted under 35 U.S.C. 154(b) by 244 days.

(21) Appl. No.: 16/864,720

(22) Filed: May 1, 2020

(65) Prior Publication Data

US 2020/0350063 A1   Nov. 5, 2020

Related U.S. Application Data

(60) Provisional application No. 62/842,902, filed on May 3, 2019.

(51) Int. Cl.
*G16H 40/20* (2018.01)
*G16H 50/20* (2018.01)
(Continued)

(52) U.S. Cl.
CPC ........... *G16H 40/20* (2018.01); *G06T 7/0014* (2013.01); *G06T 7/70* (2017.01); *G16H 10/60* (2018.01);
(Continued)

(58) Field of Classification Search
CPC ........ G16H 40/40; G16H 10/60; G16H 50/20; G06T 7/70; G06T 7/0014; G06T 2200/24;
(Continued)

(56) References Cited

U.S. PATENT DOCUMENTS

| 10,171,533 B1 | 1/2019 | Mitchell et al. | |
| 2008/0169931 A1* | 7/2008 | Gentry | G08B 21/22 600/300 |
| 2013/0173287 A1* | 7/2013 | Cashman | H04N 7/141 705/2 |
| 2013/0204145 A1* | 8/2013 | Shah | A61B 5/0205 709/201 |

(Continued)

FOREIGN PATENT DOCUMENTS

| WO | 2012037192 | 3/2012 |
| WO | 2020227128 | 11/2020 |

OTHER PUBLICATIONS

"International Application Serial No. PCT US2020 031119, International Preliminary Report on Patentability dated Nov. 18, 2021", 14 pgs.

(Continued)

*Primary Examiner* — Terrell M Robinson
(74) *Attorney, Agent, or Firm* — Schwegman Lundberg & Woessner, P.A.

(57) ABSTRACT

A system and method are provided for performing operations comprising: receiving one or more images from an image capture device of a medical treatment location; applying a trained machine learning model to the one or more images to detect presence of a patient in the medical treatment location, the trained machine learning model being trained to establish a relationship between one or more features of images of the medical treatment location and patient presence; generating context assessment for the medical treatment location based on the detected presence of the patient; and transmitting, over a network, the context assessment for presentation on a user interface of a client device.

19 Claims, 8 Drawing Sheets

(51) Int. Cl.
G16H 10/60 (2018.01)
G06T 7/00 (2017.01)
G06T 7/70 (2017.01)
(52) U.S. Cl.
CPC ......... *G16H 50/20* (2018.01); *G06T 2200/24* (2013.01); *G06T 2207/20081* (2013.01); *G06T 2207/30004* (2013.01); *G06T 2207/30196* (2013.01); *G06T 2207/30244* (2013.01)
(58) Field of Classification Search
CPC . G06T 2207/20081; G06T 2207/30004; G06T 2207/30196; G06T 2207/30244
See application file for complete search history.

(56) References Cited

U.S. PATENT DOCUMENTS

| 2015/0081322 | A1* | 3/2015 | Woolford | G16H 30/20 |
| | | | | 705/2 |
| 2017/0161443 | A1* | 6/2017 | Bassham | G16H 40/20 |
| 2018/0330815 | A1 | 11/2018 | Demir et al. | |
| 2019/0057775 | A1* | 2/2019 | Purusothaman | H04L 63/04 |

OTHER PUBLICATIONS

"International Application Serial No. PCT US2020 031119, International Search Report dated Aug. 11, 2020", 5 pgs.
"International Application Serial No. PCT US2020 031119, Written Opinion dated Aug. 11, 2020", 12 pgs.

* cited by examiner

CONTEXT AND STATE AWARE TREATMENT ROOM EFFICIENCY

CROSS-REFERENCE TO RELATED APPLICATION

This application claims the benefit of U.S. Provisional Application No. 62/842,902, filed May 3, 2019, which is hereby incorporated by reference in its entirety.

BACKGROUND

The hospital operating room is both a significant cost and profit center for the hospital. With increasing pressure on staff to do more with less, there is a trend towards increasing the efficiency and utilization of operating room staff and resources. The ultimate goals are to perform safe and efficient procedures, while maintaining staff satisfaction, and reducing costs and/or increasing profits.

BRIEF DESCRIPTION OF THE DRAWINGS

The foregoing and other objects, features, and advantages of the disclosure will be apparent from the following description of particular implementations, as illustrated in the accompanying drawings. The drawings are not necessarily to scale, emphasis instead being placed upon illustrated the principles of the disclosure.

DETAILED DESCRIPTION

The description that follows includes systems, methods, techniques, instruction sequences, and computing machine program products that embody illustrative implementations of the disclosure. In the following description, for the purposes of explanation, numerous specific details are set forth in order to provide an understanding of various implementations. It will be evident, however, to those skilled in the art, that implementations may be practiced without these specific details. In general, well-known instruction instances, protocols, structures, and techniques are not necessarily shown in detail.

One way to improve efficiency and utilization of an operating room is to measure certain key milestones throughout the day, across all operating rooms. Once baseline metrics have been established, it is then possible to determine where improvements can be made, and to measure those improvements. Traditional solutions attempt to measure the key milestones that are used to understand the efficiency and utilization of a particular perioperative department. Often times, these solutions burden the staff with the requirement to enter data into a 'tracking' or electronic medical record (EMR) charting system and/or to collect the data manually. Also, with these systems, the calculated results are only as good as the data that is collected. A system that requires additional data entry from an already overburdened staff, often results in inaccurate data. This happens because the data is often entered into the tracking system well after the procedure has been completed. In some cases, this data-entry work needs to be completed after cases have been completed, which can result in additional overtime expenses.

Other more semi-automated solutions might include fairly expensive third-party patient tracking systems, which leverage radio-frequency identifier (RFID) or Bluetooth infrastructure technologies. These other approaches require specialized hardware cameras, sensors, RFID tags, and various other medical equipment, which makes them less scalable and less efficient to deploy and use, and increases the overall cost of the system. This makes such approaches less desirable and adds additional burdens on the system.

The disclosed implementations improve the efficiency of using an electronic device and the efficiency and utilization of medical treatment locations by automatically generating and providing context assessment for the medical treatment location (e.g., a hospital operating room, doctor's office, waiting rooms, video device connection state, video device disconnection state, procedure information, and so forth). Specifically, the disclosed implementations receive images and/or videos from image capture devices (which are generally already installed in most treatment locations) and telemetry streams and apply such information to a trained machine learning model. The trained machine learning model recognizes relationships between one or more features of the received information of the medical treatment location and patient presence. Using an estimated output of the machine learning model indicating patient presence, the disclosed implementations can quickly, efficiently and with minimal cost provide context assessment for the medical treatment location, such as patient arrival time and departure times at the medical treatment location, video device connection state, video device disconnection state, procedure information, presence of a doctor at the medical treatment location, condition of a cut being open or closed, presence of cleaning staff at the medical treatment location, readiness of the medical treatment location, and so forth. This significantly improves the efficiency and utilization of medical treatment locations, such as operating rooms, waiting rooms, and so forth. Also, by utilizing hardware that is already available generally in medical treatment locations, the extra cost of adding specialized RFID tags and sensors on medical equipment, such as a gurney, can be avoided which reduces the overall resources needed to accomplish the disclosed task.

Figure 1:
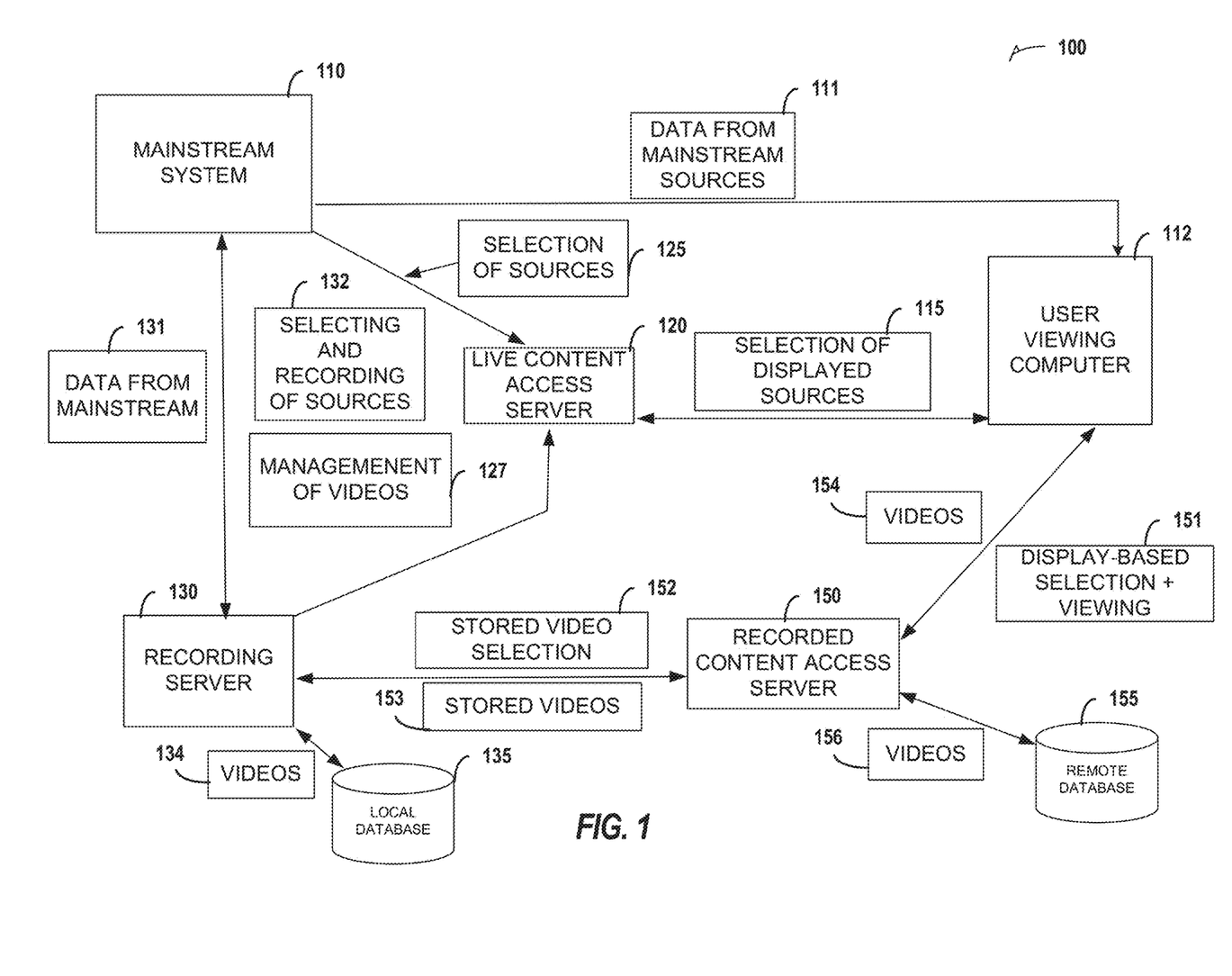
FIG. 1 is an overview block diagram showing the overall components of system for controlling communication in a medical environment according to some implementations.

FIG. 1 is an overview block diagram showing the overall components of a control system 100 for controlling communication in a medical environment, including one or more medical treatment locations, and the relative interaction therebetween. The control system 100 includes a mainstream system 110, a live content access server 120, a recording server 130, and a recorded content access server 150.

The mainstream system 110 controls the sources (e.g., image capture devices, such as cameras, and telemetry devices) in the medical treatment location (e.g., operating or medial room) and provides data from the sources, via datastream 111, to a user viewing computer 112 where the connections are brokered by the live content access server. The user viewing computer is a remote viewer who receives data from the sources in the room but may not have control over the sources in the room. A display-based system is created such that the available displays of the sources are provided to the user viewing computer 112.

A user can select a source from the sources in the medical treatment location and the content is provided to the user for viewing in a particular display. A user viewing computer 112 selects one (or a plurality) of displays that are available in a medical treatment location via datastream 115, which is interpreted by the live content access server 120 to select the sources via datastream 125 in the mainstream system 110. The available content sources are then displayed to the user viewing computer 112 so as to create a virtual presence in the room for a remote viewer, as though they are within the mainstream system 110.

In some implementations, a processor on which a machine learning model is implemented is trained to select one or more of the sources in the medical treatment location via the datastream 125. The processor receives the content from the selected sources and provides to machine leaning model the content. The machine learning model is trained to process the content from the selected sources to automatically generate a context assessment for the medical treatment location based on estimating presences of a patient at the medical treatment location. The context assessment can include any combination of patient arrival time and departure times at the medical treatment location, video device connection state, video device disconnection state, procedure information, presence of a doctor at the medical treatment location, condition of a cut being open or closed, presence of cleaning staff at the medical treatment location, readiness of the medical treatment location. The context assessment is then transmitted over a network for presentation on a user interface of a client device, such as on the user viewing computer 112. Further details of training the machine learning model are provided below in connection with FIG. 3.

Performing medical procedures requires an extensive amount of preparation by a team of medical professionals, before any type of treatment can even begin. A high-level view of the major stages of a procedure includes: 1. Room Cleaning by environmental services/housekeeping team; 2. Room preparation by scrub and/or circulating nurse (sterile field, surgical instruments, etc.); 3. Anesthesia/monitoring system setup; 4. Register patient; 5. Activate Patient Greeting System; 6. Patient arrival; 7. Patient Preparation: cleaning, draping, anesthesia, etc.; 8. Doctor arrival; 9. Perform timeout; 10. Begin procedure (cut, operate); 11. Monitor sterile field, once it has been established; 12. Finish procedure/closing; 13. Doctor departure; 14. Patient departure; and 15. Return to room cleaning. Improving the efficiency of this process can result in time savings, staff and patient satisfaction improvements, which can translate into monetary savings and the potential for increased revenues. According to the disclosed implementations, the machine learning model is trained to determine a context assessment that indicates which of the major stages of a procedure a medical treatment location is currently in based on estimating patient presence at the location (e.g., whether a patient has arrived, whether a patient has departed, status of the patient, whether a nurse has arrived/departed, whether a doctors has arrived/departed, whether cleaning crew has arrived/departed, video device connection state, video device disconnection state, procedure information, or any combination thereof). A processor can receive the output of the machine learning model and can measure time between each of the stages and durations of the stages to compute efficiency of a medical treatment location and/or efficiency of non-patient personnel (e.g., doctors, nurses, cleaning crew, hospital staff, and so forth).

Example implementations apply machine learning model(s) to one or more sources of data (e.g., video and telemetry information) to continuously monitor status of medical treatment locations in order to develop insights and awareness of operating room state, workflow efficiency and utilization. For example, example implementations may leverage one or more of the following key content sources: a first video camera directed at an entry door to the medical treatment location to monitor patient arrival, departure and to count people entering and leaving the medical treatment location throughout a medical procedure; a second video camera directed at the general state of the patient and sterile field area, including the instrument table (e.g., in some cases this camera includes a tracking device to continuously adjust the angle to track the patient throughout the medical procedure); one or more microphones listening for audio cues, such as the inception or completion of Timeout, as well as the 'mood' or stress level of the room; machine and user interface telemetry data from the point-of-care room integration system; and medical virtual presence technology which enables direct physician visualization of the room and communication with the care team during the setup/induction phase of the procedure, prior to physician arrival. These data feeds may be processed and analyzed, in real-time, by the machine learning model to generate insights to notify stakeholders (e.g., non-patient personnel) of room state changes and estimated procedure times, in order to facilitate more efficient workflow of the entire patient journey.

In addition, example implementations may generate, as part of the context assessment of the medical treatment room, milestone data during medical procedures which may be analyzed and used to develop further insight into perioperative efficiency which, in turn, then may be used by the management team to more efficiently allocate the scarce resources available to them. For example, example, the milestone data may include: Wheels In to Wheels Out=Procedure time; Wheels In vs Scheduled start time (variance); and Wheels In to Timeout=Patient Prep time and Surgery Start. The milestone data can be used to track procedure time by surgeon/procedure over time and to make recommendations on block time schedule per physician and to compare procedure time by surgeon/procedure to others. The milestone data may include Wheels Out to Wheels In=Turnover time which can be benchmarked against standards (25 to 35 min turnover) and can track turnover time by next procedure type over time; turnover=Cleaning+Preparation+Delay; measure by surgeon and/or procedure type; and detect arrival/departure of environmental services/cleaning crew. The milestone data may also include a count of the people in the medical treatment location at regular intervals (e.g., 10-30 seconds) to determine the number of times doors are opened and to correlate against the procedure time and infection rate.

The milestone data may also include case volume (e.g., average number of cases per month or year, case minutes by hour of the day, and to generate case trends). The milestone data may also include utilization analysis of the medical treatment location (e.g., operating room utilization for each day of the week, block utilization measured by surgeon or specialty service, case time and turnover time divided by the total block minutes, and off hours surgery including volume or percentage of surgeries performed during evening, nights, weekends, holidays and so forth). The milestone data may also include operational indicators (e.g., the first case start time accuracy, percentage of first cases that start within 15 minutes of scheduled time, prior to 9 AM, regular case start time accuracy, percentage within 15 minutes of schedule, same day cancellation rate, add-ons, root cause of delays, such as late staff, missing equipment, late patient, and so forth). The milestone data may also include longer term indicators (e.g., over time developing a de-identified datastore that contains the expected procedure durations by doctor/procedure including averages, expected turnover performance, accurate insight into root causes of procedure delays, and using actual measured physician/procedure time to calculate and recommend block time assignments to eliminate wasted block time).

The context assessment generated by the machine learning model can be used to identify when the patient arrives/departs to determine the total patient time in the procedure room for a particular procedure, to compare to anesthesia time, and to notify a doctor when room and patient are ready, and to compare to the scheduled start time to determine medical procedure efficiency. The context assessment generated by the machine learning model can be used to identify when the doctor arrives/departs to determine how much time it takes the physician to perform a particular procedure and how long after the patient was prepped it took for the doctor to arrive. The context assessment generated by the machine learning model can be used to identify when the anesthesiologist arrives/departs to determine a case delay factor; to identify when the instrument tray arrives from sterile processing to determine a case delay factor; to determine when the room is ready for use (clean, equipment ready, staff present) to determine room utilization and efficiency; determine when the patient is awake or asleep to determine how long the patient was under anesthesia for a given procedure and to notify housekeeping to clean the room; determine when the cleaning crew arrives/departs to determine room turnover time as a calculation of utilization and efficiency; determine when the room is vacant to determine room utilization and reduce power consumption; to count people in the medical treatment location to determine average and peak people in the location and the number of times the doors are opened to correlate the information with infection rate; detect open/closing time to detect when the skin is first cut (which indicates completion of timeout) and when the incision is closed; and to track equipment.

With the detection of the Wheels In event, such as when the machine learning model detects initial presence of the patient in the medical treatment location, the disclosed implementations identify that the patient is in the room and can notify the surgeon that his/her patient has arrived in his operating room. This may be done using a premise-based, cloud platform, or hybrid solution, with one or more connected mobile applications.

At the end of the medical procedure, such as when the machine learning model detects that the patient is no longer in the medical treatment location (e.g., has been wheeled out of the room), the disclosed implementations may send additional notifications to other stake holders (environmental services, PACU, setup team, etc.) to prepare them to receive the patient, and/or to arrive on time to perform their designated tasks. For example, notifications can be automatically generated and sent to the designated stakeholders, including: alerting a surgeon w/sterile field photo when patient arrives; alerting PACU when closing/extubation begins; alerting housekeeping/environmental services when closing/extubation is underway and/or when the patient leaves the room; alerting a charge nurse if procedure is running longer than expected; alerting the next surgeon if previous procedure is running longer than expected; and/or alerting the setup team when cleaning is complete. FIG. 4 illustrates a schematic diagram showing workflow-based messaging according to some implementations. The schematic diagram shown in FIG. 4 demonstrates various treatment room context assessments 401 that can be generated based on processing medical treatment location images and/or telemetry information associated with the medical treatment location.

Figure 4:
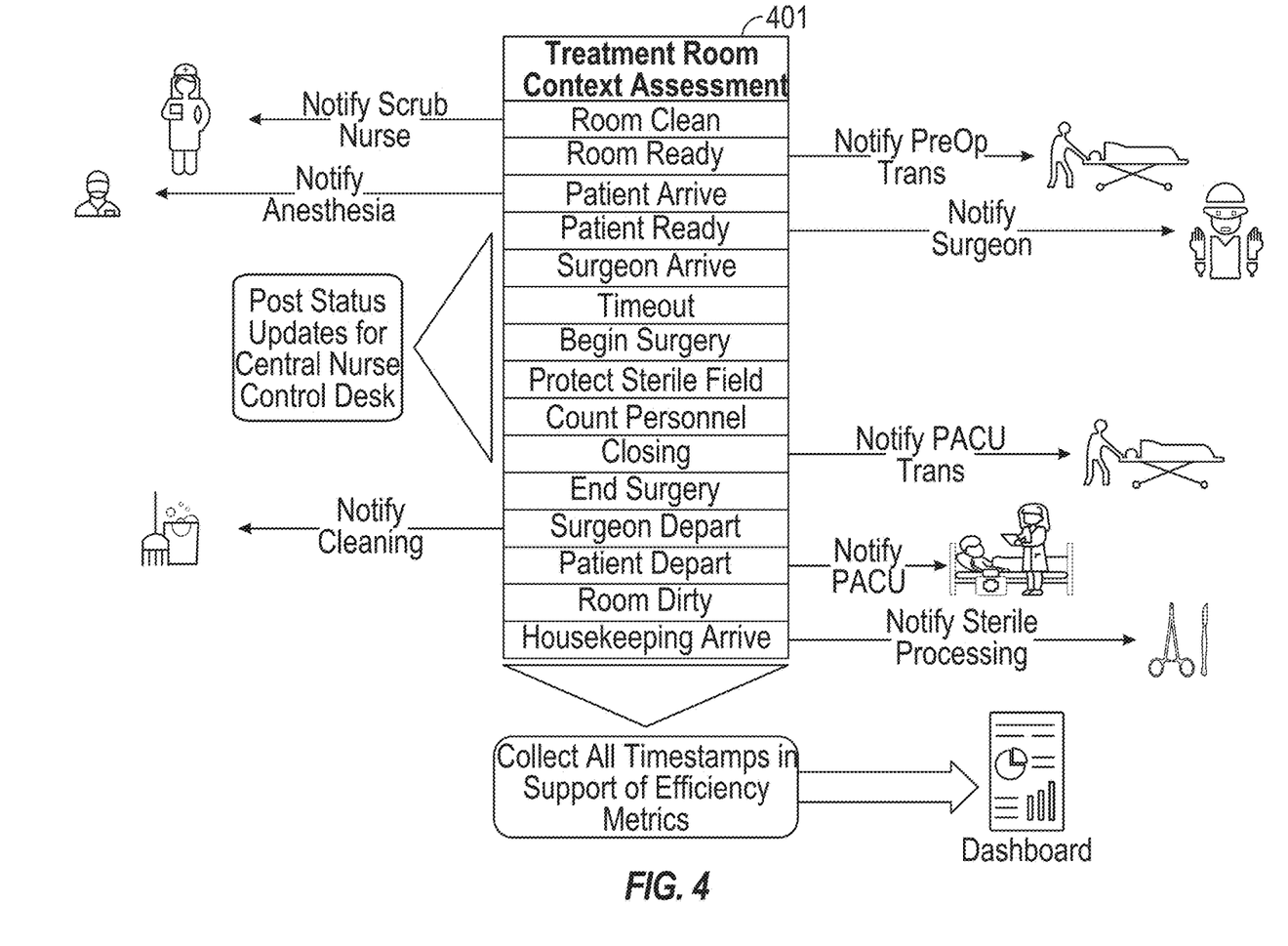
FIG. 4 illustrates a schematic diagram showing workflow-based messaging according to some implementations.

The disclosed implementations may deliver the notifications, as shown in FIG. 4, to the stakeholders on respective computing devices of the stakeholders. In other implementations, the notifications may be delivered as alerts through multiple alternate communication channels. For example, video status boards may be used at central nurse stations and in doctors' lounges and can be designed to provide a composite live view of all operating rooms on one or more displays and/or via mobile applications. The room status updates or context assessments and notifications of the context assessments can be provided through the status board channel. An illustrative status board channel 701 is shown in FIG. 7. Each window represents a live video feed from the designated medical treatment room. Clocks 702 may represent an estimation of procedure completion time, according to example implementations, where yellow and red highlights indicate (for example) a projected case delay.

Figure 7:
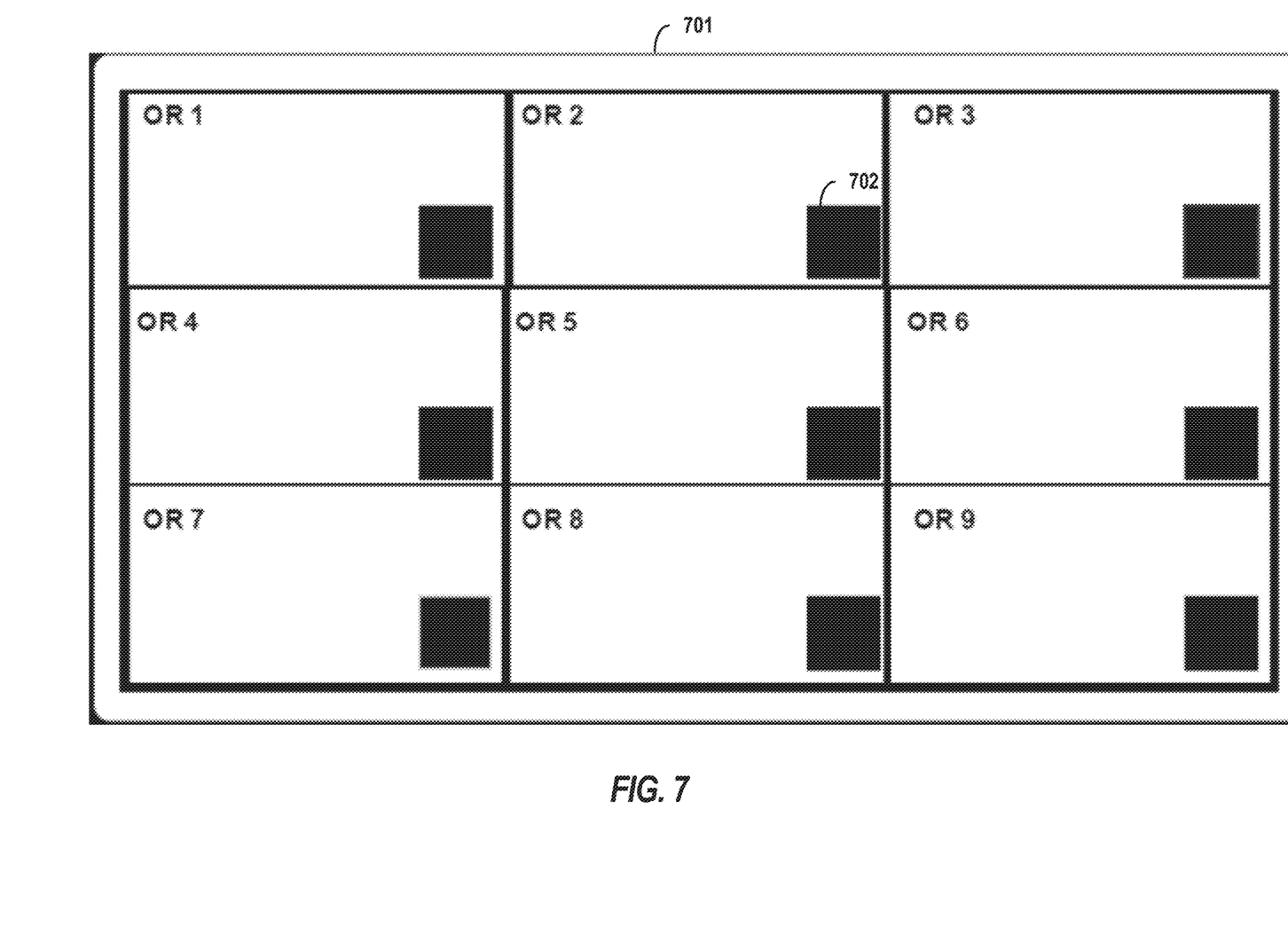
FIG. 7 is a diagram illustrating an example of a status board indicating video feed for a set of operating rooms according to some implementations.

Reference is now made to FIG. 1A showing a schematic floor plan view of a patient in a medical treatment location of a medical environment. As shown, the medical treatment location 160 has a patient 162 therein, and the medical treatment location 160 includes a plurality of cameras 165, 166, 167 and 168 that are used to establish a virtual presence for a remote viewer as though they are in the medical treatment location 160. In some implementations, the outputs of the plurality of cameras 165, 166, 167 and 168 are provided to a trained machine learning model to automatically generate context assessment for the medical treatment location 160.

Figure 1A:
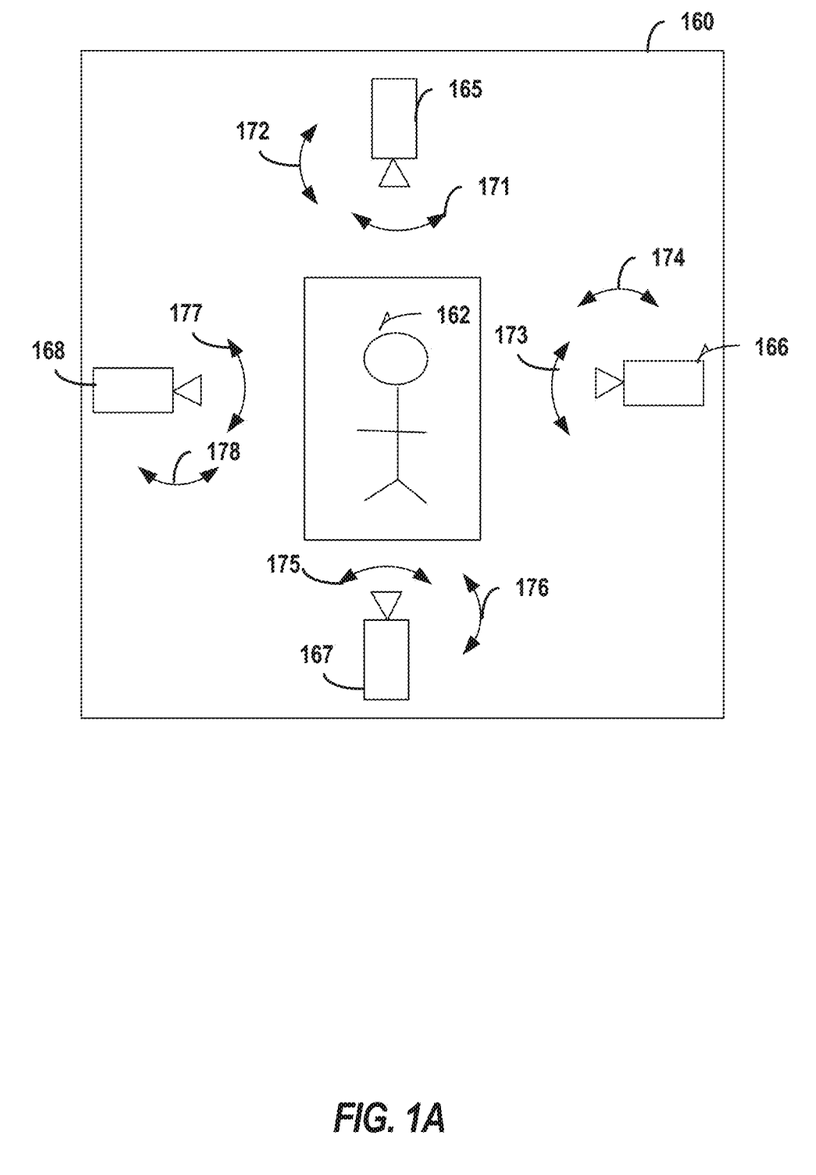
FIG. 1A is a schematic floor plan view of a patient in a room of a medical environment, including a plurality of cameras for creating a virtual presence in the room for a remote viewer according to some implementations.

Each of the cameras 165, 166, 167 and 168 can be standard pan/tilt/zoom (PTZ) cameras that move, respectively in a panning back-and-forth direction 171, 173, 175, 177 and a tilting up-and-down direction 172, 174, 176 and 178. The cameras can also zoom inward and outward in accordance with ordinary skill. The virtual presence cameras 165, 166, 167 and 168 provide a full 360-degree view of the medical treatment location 160 such that a remote viewer is able to view any angle and perspective of the patient during a medical procedure. More specifically, when a remote viewer establishes a connection to create the virtual presence, the viewer is first presented with a 360-degree view of the room to have a "lay of the land" perspective of the overall room. Once the user has the 360-degree view of the room, they are given a list of available displays, based upon the context of the room. As described in greater detail herein, the context of the room automatically determines the content that is available to the local user as well as the content available to remote viewers. Although four cameras are depicted in the medical treatment location 160, any number of cameras from one camera to tens or hundreds of cameras can be employed to establish the virtual presence. The number of cameras is variable within ordinary skill depending upon the size of the room, the number of staff generally present within the room, and other factors readily apparent and applicable by those having ordinary skill in the art.

In some implementations, each camera of the cameras 165, 166, 167 and 168 is associated with a different viewing angle. The viewing angle is stored in association with each of the cameras and is provided as some of the information and content to the machine learning model. In some cases, depending on the angle of the camera, a given machine learning model of a plurality of machine learning models is selected. Namely, each machine learning model may be trained to generate context assessment based on estimating patient presence using images captured from a respective angle. For example, a first machine learning model is trained to generate context assessment based on estimating patient presence using images captured from a first angle (relative to a floor surface normal) in the medical treatment location (e.g., an overhead straight down view, such as a birds-eye-view). A second machine learning model is trained to generate context assessment based on estimating patient presence using images captured from a second angle (relative to a floor surface normal) in the medical treatment location (e.g., an across the room view). A processing device, such as user viewing computer 112, receives a video stream from a first camera 165 and determines that the first camera 165 is associated with the first angle. In response, the processing device provides the video feed from the first camera 165 to the first machine learning model rather than the second machine learning model to obtain the context assessment for the medical treatment location.

In some cases, rather than multiple distinct cameras 165, 166, 167 and 168 in the medical treatment location, a single panoramic camera can be used in the medical treatment location. A single panoramic camera can provide a plurality of angles that the multiple cameras 165, 166, 167 and 168 provide. In such cases, each portion of the panoramic image provided by the panoramic camera can be labeled or tagged with a particular angle or view. The labeled or tagged angle or view can be provided along with the images captured by the camera to the processing device to select and apply a machine leaning model to generate the content assessment for the medical treatment location.

In some cases, faces are detected in the video streams provided by the cameras 165, 166, 167 and 168 and are masked or de-identified to support patient and staff privacy. The masks or de-identification tracks the object as the object moves throughout the medical treatment location. In some cases, additional sources of data (e.g., microphones) are deployed in the medical treatment location to provide audio information to the machine learning model for generating context assessment. For example, the machine learning model is trained to recognize wake-up key phrase, respond to commands (capture image, start recording, bookmark, etc.), recognize specific voices (doctor in the room), index the audio track of an entire video recording, making it searchable, post case. The detection of a doctor's voice in the audio feed can be used by the machine learning model to generate the milestones, such as detecting when the medical procedure begins/ends and how long the doctor spends in the room.

Referring back to FIG. 1, the mainstream system 110 also transmits data from the mainstream (in-room) active sources to a recording server 130 via datastream 131. The selecting and recording of active sources in the room is performed via datastream 132, and then data is transmitted via datastream 131 to the recording server 130. The control system 100 operates such that the selecting of active sources in the room is performed on the displays of the sources that are exclusively controlled by a local mainstream user within the mainstream system 110. Additionally, the virtual presence cameras (for example 165, 166, 167, 168 of FIG. 1A), allow a user to view the entire medical treatment location from a 360-degree perspective as though they are in the center of the medical treatment location, without having to enter into the medical environment. This can save critical time and space needed during a medical procedure, as well as reduce the risk of infection to the patient.

The displays and sources are collectively referred to as "content" herein. The content assessment of a medical treatment location can automatically be determined by the context of the room. The context assessment refers to the type of procedure, the status of the room, the state of the patient, equipment status, and determines a higher level of abstraction of a procedure to thereby determine the content (e.g., device) for a particular procedure. As described in greater detail with reference to FIGS. 3-5, the context assessment for a medical treatment location can be automatically determined based upon images, videos, telemetry streams, or any combination thereof transmitted within the medical environment network.

Figure 3:
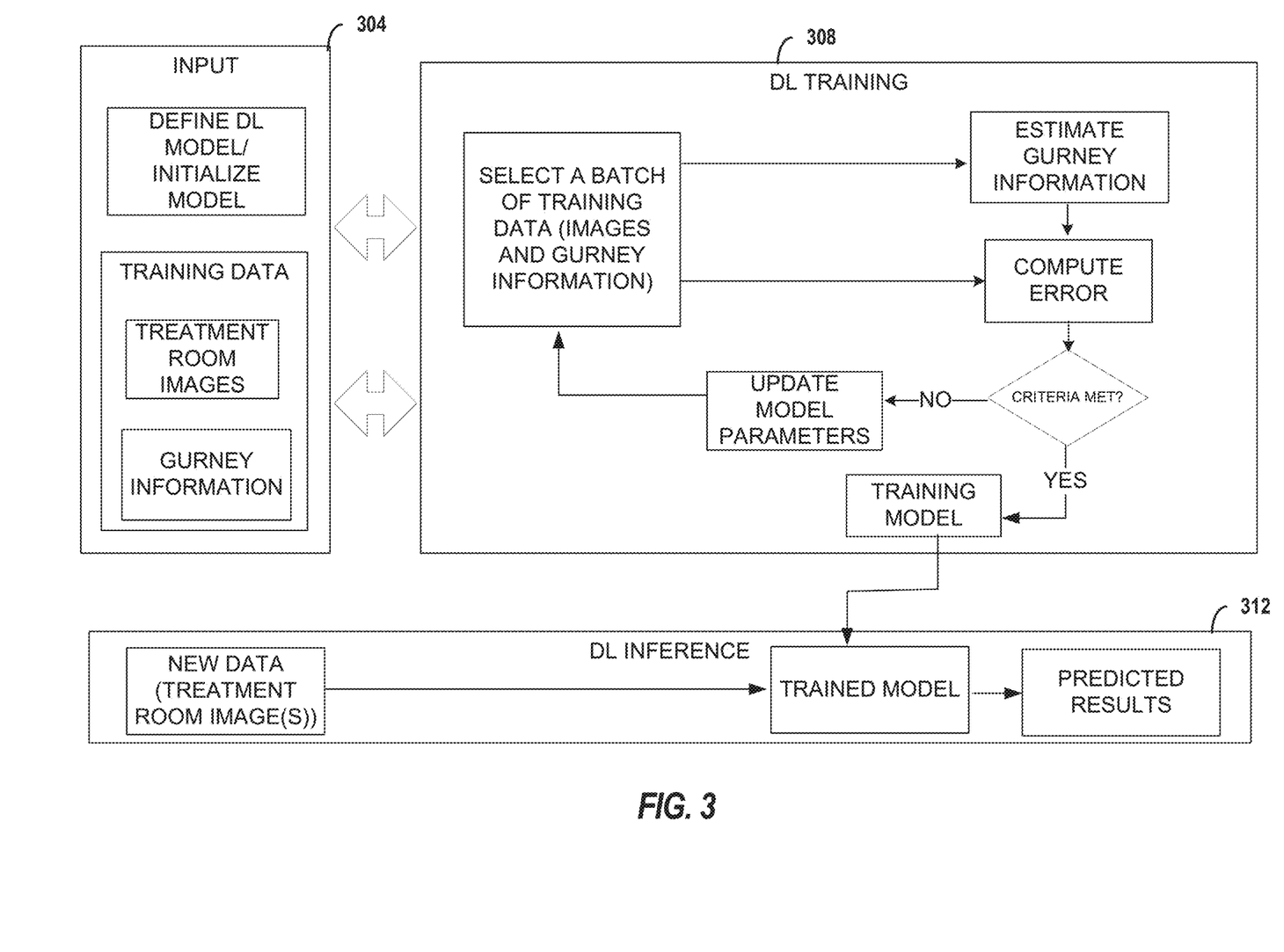
FIG. 3 illustrates an exemplary flow diagram for deep learning according to some implementations.
Figure 5:
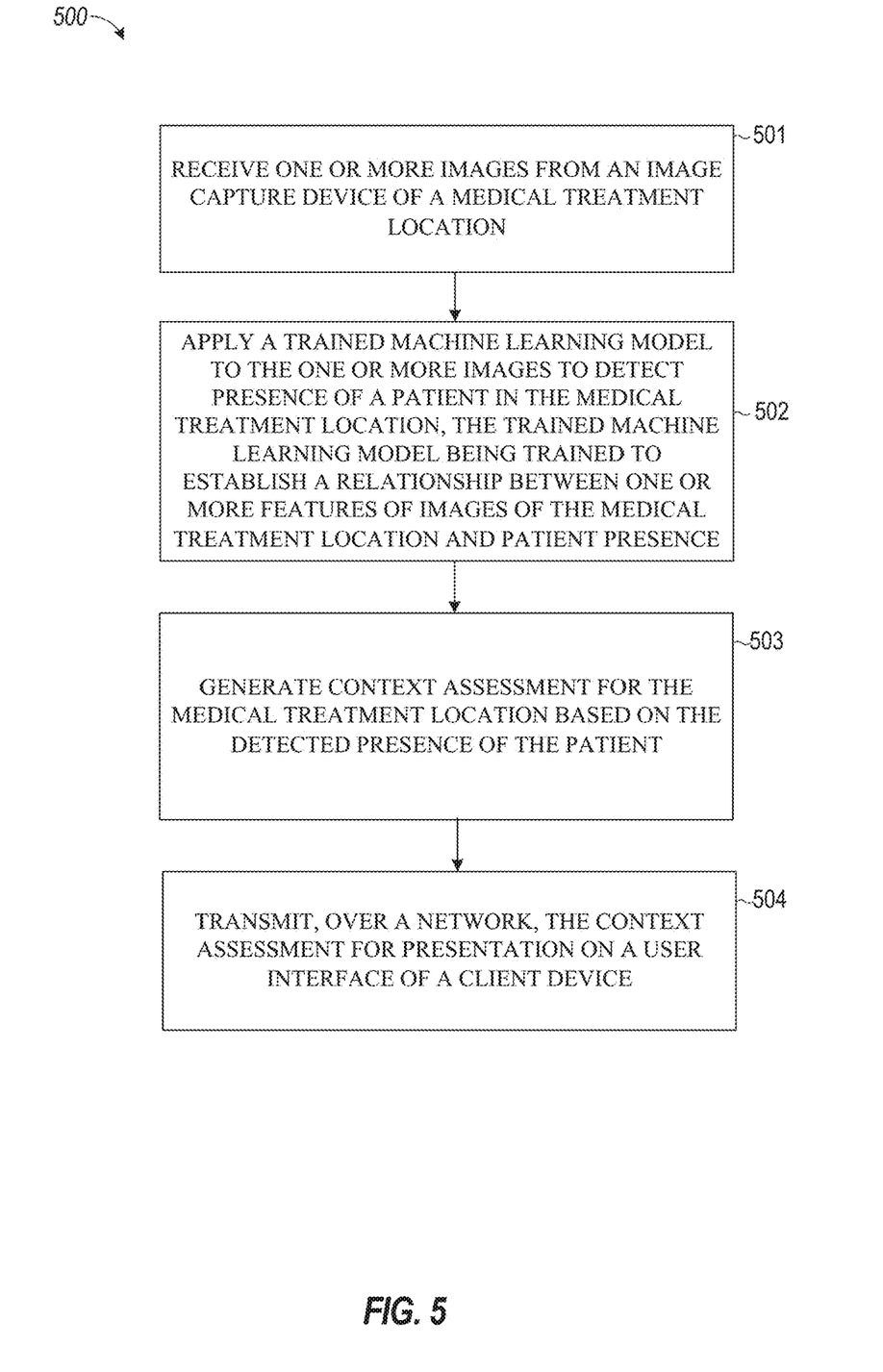
FIG. 5 illustrates a flow diagram of operations for generating a context assessment for a medical treatment location according to some implementations.

Live videos and/or recorded videos (on the recording server 130) are accessed via datastream 127 by the live content access server 120. The live content access server 120 is a broker or electronic device that controls access to live audio or video content. This enables a remote viewer to access both live and recorded video files. Remote viewer in this disclosure refers to a user of a computing device, a processor at a computing device, or any combination thereof. In some implementation, the recorded content access server 150 receives requests from a user or processor at user viewing computer 112 via datastream 151 to select and view data stored in the recording server 130. Recorded content access server 150 is a broker or electronic device that enables remote users to access previously stored and indexed audio or video content. In some cases, the live content access server 120 and the recorded content access server 150 are implemented by the same device. In some cases, the live content access server 120 and the recorded content access server 150 are implemented by one or more distinct devices.

The recorded content access server 150 selects stored videos and data via datastream 152 to be accessed by the recording server 130. The stored videos and data are transmitted to the recorded content access server 150 via datastream 153 and then provided to the remote user or processor at user viewing computer 112 via datastream 154. In this manner, a user or processor at a viewing computer can view both live and stored video and data based upon the sources available within the mainstream system 110.

A user or processor also has access to an optional second set of sources (e.g., telemetry sources, such as EMR data, an audio stream of the medical procedure, patient scheduling information, and/or patient registration information) that can be remotely selected. The data from the mainstream system, including videos and other data, is transmitted from the recording server 130 via datastream 134 into a local database 135. This allows the videos to be stored in local database. Simultaneously, videos can be transmitted to a remote database 155 via datastream 156.

Reference is now made to FIG. 2, a network diagram showing the relative connectivity of the overall components of the system within the medical environment. Each medical treatment location (e.g., treatment (Operating) room One 201, treatment (Operating) room N 202 and Specialty Area room 203) includes a mainstream system (110 of FIG. 1) to standardize communication within the system. Each medical treatment location includes a video router 210 having a plurality of sources 211-220, 222-224, 226, 227 (a camera 211, camera 212, medical device 213, monitor 214, monitor 215, camera 216, camera 217, medical device 218, monitor 219, monitor 220, camera 222, camera 223, medical device 224, monitor 226 and monitor 227).

Figure 2:
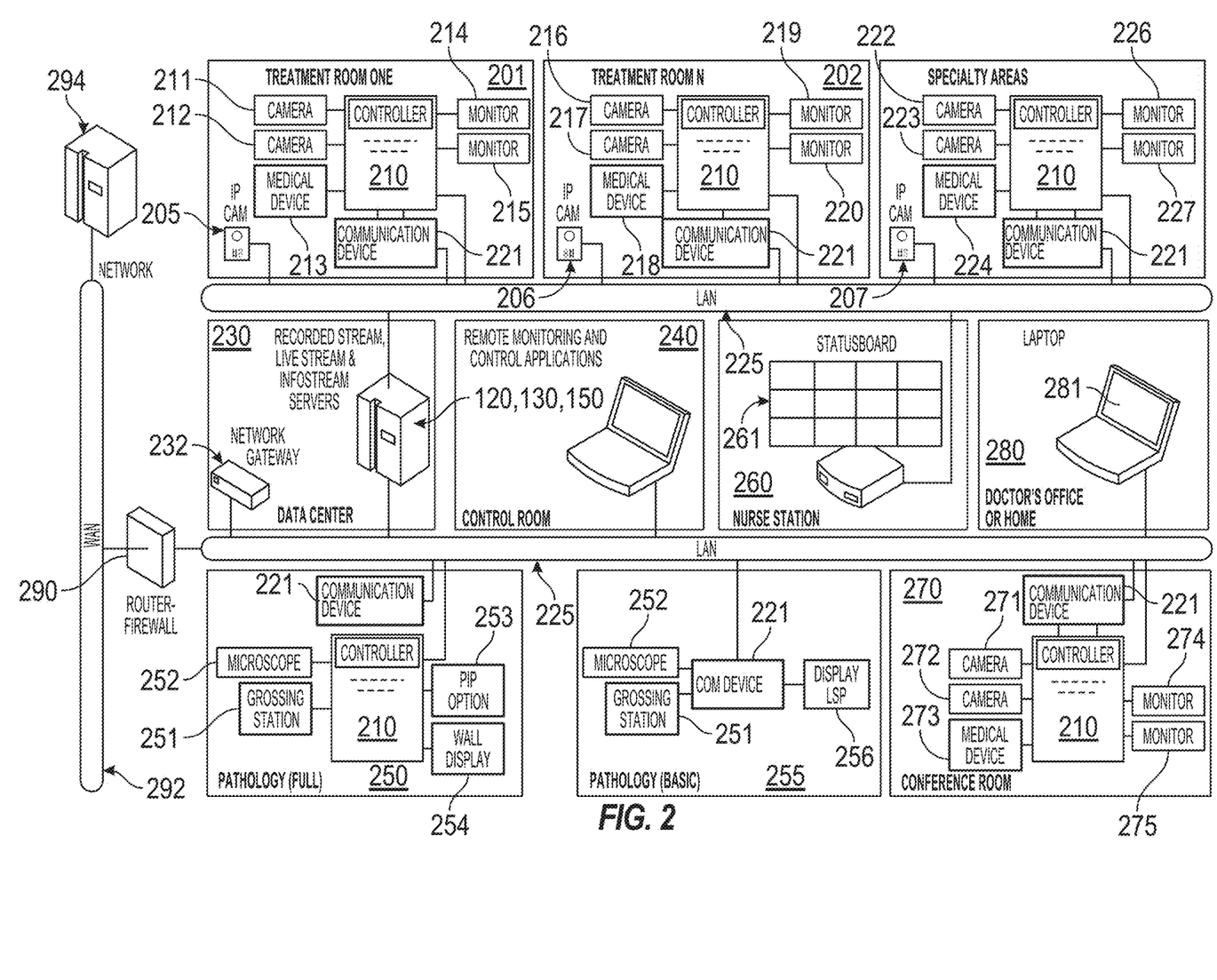
FIG. 2 is a network diagram showing the relative connectivity of the overall components of the system within the medical environment according to some implementations.

In accordance with the illustrative implementations, the plurality of sources are controlled exclusively by the local user during a medical procedure such that the remote viewer controls not the plurality of sources, but instead access to the sources via accessing the displays used during the medical procedures. The router 210 and a communication device 221 (e.g., a network interface card/device, a wireless communication device, a wireline communication device, a powerline communication device, and so forth) are connected through a LAN 225, such as a Local Area Network (LAN) or other medical environment network, to a Data Center 230, which includes the recorded content access server 150, live content access server 120, and recording server 130. Alternatively, all or part of the system can be interconnected using a wide area network (WAN). For example, one or more users can be in a site that is accessed over the Internet. Appropriate security, such as a Virtual Private Network (VPN) can be implemented to secure all or part of the Network in accordance with ordinary skill. Additionally, while not shown, the Internet can include appropriate security measures to comply with medical standards such as HIPAA (Health insurance Portability and Accountability Act). HIPAA standards address the security and privacy of health data.

The Data Center 230 can also include a network gateway 232 operatively connected to the servers 120, 130, 150. The network gateway 232 has a virtual presence application running thereon that provides a virtual view to a remote viewer (for example on the network gateway 294). The virtual view can be established on the network through video received from the virtual presence cameras (e.g. 205, 206, 207 or 165, 166, 167) located in one or more medical treatment location(s) of the medical environment. The virtual view can be a 360-degree view from combined camera views in accordance with ordinary skill. A "platform" as used herein refers to a hardware architecture and software framework that allows software, particularly application software, to run. Typical platforms include computer architecture, operating systems, programming languages, related user interface, and other platforms known in the art and readily applicable to those having ordinary skill.

The operating rooms (treatment rooms) 201, 202 and specialty area room 203 can also be connected through the LAN 225 to a control room 240 for remote monitoring and control applications. The control room 240 is employed in alternate implementations for external control of the mainstream systems, as desired. Various other components and entities of the medical environment can also be connected through the LAN 225, including a full pathology room 250, a basic pathology room 255, a nurse station 260, a conference room 270 and a doctor's office 280. Medical treatment location can include any one or combination of an operating room, basic pathology room, a nurse station, a typical conference room, and a doctor's office.

The pathology room 250 is similar to any operating room in the control system, and includes a mainstream system for standardizing communication between sources within the room and overall communication. The pathology room 250 includes a router 210, operatively connected to a grossing station 251, a microscope 252, a PIP (picture-in-picture) option 253, and a wall display 254. A communication device 221 is provided for appropriate connectivity to the LAN 225. LAN 225 may be a wireline, powerline, wireless or any other suitable communications network. The pathology room 250 is a full pathology room showing many available functionalities and hardware components available using the mainstream system. A basic pathology room 255 can also be employed, which includes a grossing station 251, a microscope 252, and a display (LSP) 256. A communication device is capable of receiving two streams of input and converting into multiple streams.

The communication device converges the recording and streaming so that the streams are sent to the server and the recording is sent to the server. The communication device is capable of taking a single video input and turning it into three outbound streams of different resolution. For example, the communication device can take a single input stream and convert into a 480p, 720p and 1080p resolution output. The illustrative system employs a spatial matrix from a single stream to provide multiple output streams at varying resolutions. Multiple output streams at different resolutions is particularly useful in the medical context where the output stream can be predetermined based upon the particular source from which video is being streamed. For example, certain streams are desired to be in higher resolution, like certain streams can be in a lower resolution.

The nurse station 260 is also in communication through the LAN 225 and includes a status board 261 that provides displays of sources to the nurse station 260. A conference room 270 is connected through the LAN 225 and includes the appropriate mainstream system for standardizing communication that includes a video router 210. The conference room 270 includes a camera 271, a camera 272, a medical device 273 and monitors 274, 275, and is appropriately connected through communication device 221 for communication through the LAN 225. A doctor's office 280 includes a laptop 281 (or other appropriate device) connected through the LAN 225 for communication with entities on the network to create a virtual presence for a remote viewer in the doctor's office, as though the remote viewer were present in the room and able to view the displays as available to the local user.

The system can also be connected through an appropriate router-firewall 290 through a WAN 292 to a network 294 to establish a virtual presence for users in the room. The virtual presence is established through the network gateway platform 232 operatively connected to system servers (e.g., 120, 130, 150). In accordance with illustrative implementations, a client application on a computing device of a remote user or remote viewer of the network 294 is employed to select a display within the room of the medical environment, after the virtual view has been provided to the remote user on the network 294. The client application can run on one or more of the disclosed servers to determine context assessment for the medical treatment location based on estimating patient presence using a machine learning model. Remote users can thereby establish the virtual presence in a medical treatment location connected to the LAN 225, including the Operating Room One 201, Operating Room N 202, Specialty Area Room 203, full pathology room 250, basic pathology room 255 and typical conference room 270. One or more servers, connected to the LAN 225, including the Operating Room One 201, Operating Room N 202, Specialty Area Room 203, full pathology room 250, basic pathology room 255 and conference room 270, can access content (e.g., video and telemetry streams) from various medical treatment locations via these sources to determine context assessment for the medical treatment locations based on estimating patient presence at the locations using one or more machine learning models.

The mainstream system 110, shown by way of example, as Operating Room One 201, Operating Room N 202, full Pathology room 250, basic Pathology room 255 and Conference Room 270 in FIG. 2, provides control of and access to in-room sources using a video matrix switch for standardizing the sources to improve communication.

FIG. 3 illustrates an exemplary flow diagram for deep learning, where a deep learning model (or a machine learning model, such as a neural network, linear regression, logistical regression, random forest, gradient boosted trees, support vector machines, decision trees, nearest neighbor, or naïve bayes), such as a deep convolutional neural network (DCNN), can be trained and used to determine presence of patient in a medical treatment location or to distinguish between patient and non-patient personnel in the medical treatment location. Based on whether a patient is detected in the medical treatment location, context assessment (e.g., wheels-in to wheels out time, medical procedure time, number of times a door is opened during a medical procedure, and so forth) can be automatically determined.

Inputs 304 can include a defined deep learning model having an initial set of values and training data. The training data can include treatment room images and gurney information. The training data can include multiple of these treatment room images for multiple types of medical treatment locations (e.g., different types of operating rooms, waiting rooms, doctor's offices, and so forth) at any number of different angles. The training data can include multiple of these treatment room images for multiple types of medical treatment locations (e.g., different types of operating rooms, waiting rooms, doctor's offices, and so forth), where different portions of a panoramic image are labeled to identify different regions or angles of the medical treatment locations. The treatment room images include a plurality of training videos, where a first set of the training videos comprises a gurney with a patient and a second set of the training videos comprises the gurney without the patient. The gurney information is associated with each of the plurality of training videos and identifies a position of the gurney in each training video. The plurality of training videos may be captured at different lighting conditions and may be adjusted by applying one or more photographic filters. The training data can include telemetry information, such as patient scheduling information, electronic medical record (EMIR) data, or patient registration information. The telemetry information can also be paired with the treatment room images and the gurney information.

The deep learning model can include a neural network, such as a deep convolutional neural network (DCNN). The deep learning network can be trained on treatment location images, such as a first set of training videos corresponding to a first angle of a camera in a medical treatment location and a second set of the training videos corresponding to a second angle of a camera in the medical treatment location. When trained, the deep learning network can produce an estimate of whether a patient is present in the medical treatment location. The expected results can include estimated location of a gurney in a medical treatment location and whether or not a patient is on the gurney and can be used to determine presence of a patient in the medical treatment location to generate context assessment for the medical treatment location. In some cases, the deep learning model considers a combination of the medical treatment location images and the telemetry information to estimate presence of a patient in the medical treatment location.

In some implementations, the medical treatment location images at different angles can be paired with gurney information for their respective angles. In such cases, rather than training the machine learning model to estimate the presence of a patient for different camera angles, the machine learning model can be trained to estimate the presence of a patient directly at for each angle of a camera. Different machine learning models can be trained for each camera angle that is available in medical treatment locations. In such, circumstances, the angle information is retrieved for a given image and the appropriate machine learning model is selected and used to detect presence of a patient.

During training of deep learning model 308, a batch of training data can be selected from the treatment room (location) images and the gurney information associated with the treatment room images. The selected training data can include at least one treatment location image (corresponding to a particular camera angle) and the corresponding ground truth gurney information for the particular camera angle. The selected training data can include multiple medical treatment location images representing views of the same medical treatment location from multiple equally spaced or non-equally spaced medical treatment location angles and the corresponding ground truth gurney information at those different equally-spaced or non-equally spaced gantry angles.

The deep learning model 308 can be applied to the selected medical treatment location images to provide estimated results (e.g., estimated location of the gurney or estimated presence of the gurney), which can then be compared to the expected results (e.g., ground truth location of the gurney associated with the selected medical treatment location images) to compute a deviation (e.g., a difference in the coordinates of the estimated location and the ground truth location of the gurney) that can provide an indication of training errors. The errors can be used during a procedure called backpropagation to correct the errors in parameters of the deep learning network (e.g., layer node weights and biases), such as to reduce or minimize errors in the gurney location estimates during subsequent trials. The errors can be compared to predetermined criteria, such as proceeding to a sustained minimum for a specified number of training iterations. If the errors do not satisfy the predetermined criteria, then model parameters of the deep learning model can be updated using backpropagation, and another batch of training data can be selected from the other medical treatment location images (of the same medical treatment location or other medical treatment locations) and expected results for another iteration of deep learning model training. If the errors satisfy the predetermined criteria, then the training can be ended, and the trained model can then be used during a deep learning testing or inference stage 312 to predict a gurney location or presence of the gurney based on medical treatment location images different from the training data. The trained model can receive new medical treatment location image(s) representing a view from a particular angle and provide predicted results (e.g., gurney location or presence for that particular gantry angle).

The gurney location or presence can be used to either infer presence of the patient in the medical treatment room or further processed to verify presence of the patient. For example, a portion the image at which the gurney location is detected can be provided to an object detection or recognition system. The object detection or recognition system can determine whether there is a person on the gurney or whether the gurney is empty. If a person is detected on the gurney, such as using face detection techniques (object recognition techniques, such as the Viola-Jones algorithm), the object detection system may indicate that there is a patient present in the medical treatment location. If a person is not detected on the gurney, the object detection system indicates that there is no patient detected in the medical treatment location.

In some cases, the trained model can receive new medical treatment location image(s) representing a view from a particular angle and provide an indication of presence of a gurney for that particular gantry angle. If the trained model indicates that a gurney is detected in the medical treatment location image(s), the trained model determines that a patient is present at the medical treatment location. If a gurney is not detected on the gurney, the trained model indicates that there is no patient detected in the medical treatment location.

FIG. 3 illustrates an implementation of a method for training a Deep Convolutional Neural Network (DCNN), such as the DCNN for determining presence of a patient at a medical treatment location based on at least one medical treatment location image. The DCNN can receive sets of medical treatment location images, in some cases representing different views of a medical treatment location from different angles. To begin network training, an iteration index can be set to an initial value of zero. A batch of training data can be formed from a subset of the received sets of medical treatment location images and corresponding gurney information. Particularly, one batch of medical treatment location images may represent a view of a door or entryway to the medical treatment location and may include some images with a gurney and some images without a gurney. The training data includes gurney information that is manually input by a user in which presence of a patient in a given image is specified and/or the location of the gurney in the image is specified.

The batch of training data can be provided to the DCNN and the DCNN parameters can be updated based thereon. The DCNN can provide an output set of gurney information or patient presence information based on current parameters of the DCNN for a given set of received medical treatment location images. A comparison can be made between the ground truth gurney information or patient presence information and the output set of gurney information or patient presence information corresponding to the received sets of medical treatment location images in the batch of training data. Corresponding error sets, where each error value can be the difference between the estimated gurney information or patient presence information and the corresponding ground truth gurney information or patient presence information are determined from the comparison. Parameters of the DCNN can then be updated based on the corresponding errors, such as by using backpropagation.

After updating the parameters of the DCNN, the iteration index can be incremented by a value of one. The iteration index can correspond to a number of times that the parameters of the DCNN have been updated. Stopping criteria can be computed, and if the stopping criteria are satisfied, then the DCNN model can be saved in a memory, and the training can be halted. If the stopping criteria are not satisfied, then the training can continue by obtaining another batch of training images and corresponding ground truth gurney information. In an implementation, the stopping criteria can include a value of the iteration index (e.g., the stopping criteria can include whether the iteration index is greater than or equal to a determined maximum number of iterations). In an implementation, the stopping criteria can include an accuracy of the output set of machine parameters (e.g. the stopping criteria can include whether the difference between the output and the ground truth information corresponding in the batch of training data is smaller than a threshold). In an implementation, the threshold can correspond to an asymptotic minimum of all errors determined.

In some implementations, a camera feed is continuously received and processed by the trained machine learning model. The trained machine learning model may process the camera feed to detect presence of the patient. In an example, the trained machine learning model initially determines that a patient is not present in the medical treatment location (e.g., based on an estimation that a gurney is absent from the camera feed or that the gurney is in a designated location where patients are not currently being treated). In such cases, the context assessment of the medical treatment location indicates that the medical treatment room is ready to receive a patient. In certain cases, when the trained machine learning model detects presence of other non-patient personnel in the medical treatment location while the patient is not present in the medical treatment location, the trained machine learning model determines that the medical treatment location is being prepped for a patient. Upon detecting at a later time a patient arriving at the medical treatment location based on the trained machine learning model processing a subsequent camera feed and detecting presence of a gurney, the system begins a timer for the medical procedure and stores the current time when the patient arrives. This timer can represent the difference between wheels-in to wheels out. Namely, at a later time after the patient arrives, the trained machine learning model detects absence of the patient in the treatment room images. In such cases, the timer is halted and the total time amount represents the amount of time the patient spent in the room. In some cases, the trained machine learning model receives telemetry information and/or audio information and uses that information to compute a further context assessment (e.g., duration of the medical procedure from when the patient is cut to when the incision is closed). In some cases, the time when the patient arrives is compared with the telemetry information indicating scheduling information to determine whether any delay exists between the scheduled arrival time and the actual arrival time to determine efficiency of the medical treatment location.

In some cases, the trained machine learning model detects audio of a physician and determines that a medical procedure as begun after the patient has arrived in the medical treatment location. At that time, the trained machine learning model selects a camera angle that is directed at the entry door to the medical treatment location. The trained machine learning model analyzes images of the entry door to count how many times during the medical procedure the entry door is opened/closed. This number of times can be correlated with any infection the patient ends up experiencing (outcome of the medical procedure) (as determined based on the EMIR data) and can be compared with the expected number of times the door is expected to be opened. In some cases, at the time of detecting that the medical procedure has begun, the trained machine learning model selects a camera angle directed at medical equipment to compute a sterilization parameter of the equipment.

FIG. 5 illustrates a flow diagram 500 of operations for generating a context assessment for a medical treatment location according to some implementations. The operations of diagram 500 can be performed by the mainstream system 110 or any other component shown in FIG. 1.

At operation 501, the mainstream system 110 receives one or more images from an image capture device of a medical treatment location. For example, images from one or more of the cameras shown in FIG. 1A may be received.

At operation 502, the mainstream system 110 applies a trained machine learning model to the one or more images to detect presence of a patient in the medical treatment location. The trained machine learning model is trained to establish a relationship between one or more features of images of the medical treatment location and patient presence. For example, a machine learning model, trained in accordance with the process described in connection with FIG. 3, is retrieved and applied continuously or periodically to the images of the medical treatment location. Specifically, the machine learning model may be trained to identify the presence of a gurney in the medical treatment location and/or the location of the gurney in the images of the medical treatment location.

At operation 503, the mainstream system 110 generates context assessment of the medical treatment location based on the detected presence of the patient. For example, the difference in time from when the machine learning model detects presence of a patient at the medical treatment location and when the machine learning model detects absence of the patient can be used to determine wheels-in to wheels out time (e.g., the total time spent by the patient at the medical treatment location).

At operation 504, the mainstream system 110 transmits, over a network, the context assessment for presentation on a user interface of a client device. For example, notifications including or indicating the context assessment can be generated and sent to the appropriate stakeholders (e.g., nurses or physicians) on their respective client devices. In another example, a status board channel 701, shown in FIG. 7, is updated to include the context assessment, such as using clocks 702 or another form of indicator in a region of the board corresponding to the medical treatment location for which the images are captured and processed to generate the context assessment.

FIG. 6 is a sample screen sequence from the mobile application, which supports the notification-based workflow described above, according to an example implementation of the present disclosure.

Figure 6:
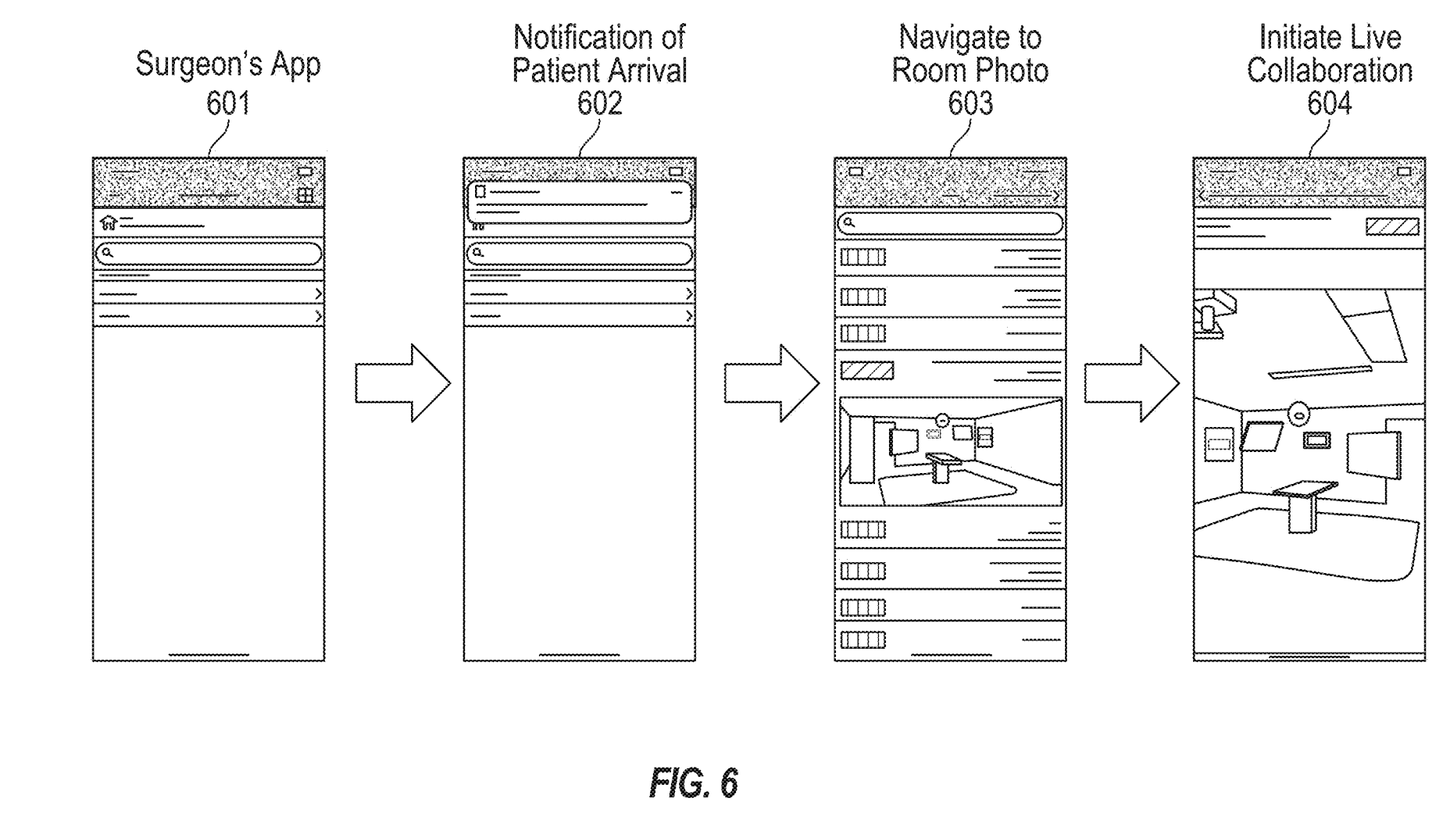
FIG. 6 illustrates screen shots from a mobile application in the notification-based workflow according to some implementations.

As illustrated in the application 601 shown in FIG. 6, the 'alert' 602 notifies the surgeon of a room state change. The photographs provide a view 603 of the room to allow the surgeon to visually evaluate room readiness. In addition, if the surgeon feels the need to communicate directly with the staff, the surgeon may initiate a live 2-way collaboration session 604 with the staff in the room with a single button click. For example, according to the disclosed implementations, a machine learning model may detect presence of a patient entering a medical treatment location. In response, the mainstream system 110 may generate a context assessment for the medical treatment location (e.g., determine that the patient is ready for a medical procedure). In such cases, the mainstream system 110 processes EMR data associated with the medical treatment location to identify the physician assigned to perform the medical procedure at the medical treatment location at the current time. The mainstream system 110 sends a notification which is presented to the physician as an alert 602. The notification may inform the physician of the status of the medical treatment location and may include the generated context assessment. The physician may select the notification and be presented with interface view 603 listing various medical treatment locations. The medical treatment location associated with the notification is automatically expanded among the list of medical treatment locations to allow the physician to view a live or recorded video of the images processed by the machine learning model to generate the context assessment. In some cases, the physician can select the displayed images to initiate live collaboration with the personnel at the medical treatment location.

Changes and modifications may be made to the disclosed implementations without departing from the scope of the present disclosure. These and other changes or modifications are intended to be included within the scope of the present disclosure, as expressed in the following claims.

What is claimed is:

1. A method comprising:
   receiving one or more images from an image capture device of a medical treatment location;
   applying a trained machine learning model to the one or more images to detect presence of a patient in the medical treatment location, the trained machine learning model being trained to establish a relationship between one or more features of images of the medical treatment location and patient presence;
   estimating a location of a gurney in the one or more images based on an output of the trained machine learning model;
   applying one or more object recognition techniques to a portion of the one or more images corresponding to the location of the gurney to determine existence of the patient on the gurney including determining whether the patient exists or fails to exist on the gurney;
   storing data indicating presence of the patient in the medical treatment location based on determining whether the patient exists or fails to exist on the gurney;
   generating context assessment for the medical treatment location based on the stored data indicating presence of the patient; and
   transmitting, over a network, the context assessment for presentation on a user interface of a client device.

2. The method of claim 1, wherein the trained machine learning model is further trained to distinguish between presence of the patient and presence of medical treatment location personnel.

3. The method of claim 1, wherein the trained machine learning model is trained by:
   receiving a plurality of training videos, a first set of the training videos comprising a gurney with a patient, and a second set of the training videos comprising the gurney without the patient, each of the plurality of training videos being tagged with information identifying the gurney;
   applying the machine learning model to a first training video of the plurality of training videos to estimate a location of the gurney in the first training video;
   obtaining the information identifying the gurney associated with the first training video;
   computing a deviation between the estimated location of the gurney in the first training video and the obtained information identifying the gurney;
   updating parameters of the machine learning model based on the computed deviation; and
   repeating the applying, obtaining, computing and updating steps for a second of the plurality of training videos.

4. The method of claim 3, wherein the plurality of training videos are captured at different camera angles using a single camera or multiple cameras, and wherein regions in a panoramic camera are designated for use as different ones of the plurality of training videos.

5. The method of claim 3, wherein the plurality of training videos are captured at different lighting conditions.

6. The method of claim 3, further comprising adjusting the plurality of training videos by applying one or more photographic filters.

7. The method of claim 1, wherein the trained machine learning model comprises a neural network, linear regression, logistical regression, random forest, gradient boosted trees, support vector machines, decision trees, nearest neighbor, or naïve bayes.

8. The method of claim 1, further comprising receiving a medical procedure stream, wherein the context assessment is generated based on the medical procedure stream and the detected presence of the patient.

9. The method of claim 1, further comprising:
determining a camera angle associated with the image capture device; and
selecting the trained machine learning model from a plurality of trained machine learning models based on the determined camera angle, each of the plurality of trained machine learning models corresponding to a different camera angle.

10. The method of claim 1, wherein the context assessment comprises patient arrival time and departure times at the medical treatment location, presence of a doctor at the medical treatment location, condition of a cut being open or closed, presence of cleaning staff at the medical treatment location, readiness of the medical treatment location.

11. The method of claim 1, wherein a medical procedure is performed at the medical treatment location, further comprising determining, as the context assessment, a number of personnel at the medical treatment location while the medical procedure is being performed.

12. The method of claim 11, further comprising receiving a telemetry stream of the medical procedure or an audio stream of the medical procedure, the telemetry stream comprising at least one of patient scheduling information, electronic medical record (EMR) data, or patient registration information.

13. The method of claim 11, further comprising determining, as the context assessment, a number of times a door to enter the medical treatment location is opened while the medical procedure is being performed.

14. The method of claim 1, wherein the context assessment comprises at least one of timeout start time, timeout finish time, video device connection state, video device disconnection state, procedure information, physician information, procedure duration, variance between a scheduled start time of the procedure and when presence of the patient is detected, or turnover time based on a determination that the patient is no longer present.

15. The method of claim 1, further comprising:
alerting one or more stakeholders about a medical procedure performed at the medical treatment location;
associating the medical procedure with one or more outcomes of the medical procedure; and
tracking medical treatment location efficiency and utilization.

16. The method of claim 1, wherein the image capture device includes at least one of:
a first video camera monitoring patient arrival, departure and people counting throughout a medical procedure;
a second video camera monitoring state of the patient and a sterile field including an instrument table;
a third video camera configured to capture different angles of the medical treatment location; or
a fourth video camera configured to capture a panoramic view of the medical treatment location and designate different portions of the panoramic view.

17. A system comprising:
one or more processors configured to perform operations comprising:
receiving one or more images from an image capture device of a medical treatment location;
applying a trained machine learning model to the one or more images to detect presence of a patient in the medical treatment location, the trained machine learning model being trained to establish a relationship between one or more features of images of the medical treatment location and patient presence;
estimating a location of a gurney in the one or more images based on an output of the trained machine learning model;
applying one or more object recognition techniques to a portion of the one or more images corresponding to the location of the gurney to determine existence of the patient on the gurney including determining whether the patient exists or fails to exist on the gurney;
storing data indicating presence of the patient in the medical treatment location based on determining whether the patient exists or fails to exist on the gurney;
generating context assessment for the medical treatment location based on the stored data indicating presence of the patient; and
transmitting, over a network, the context assessment for presentation on a user interface of a client device.

18. The system of claim 17, wherein the trained machine learning model is further trained to distinguish between presence of the patient and presence of medical treatment location personnel.

19. A non-transitory computer-readable medium comprising non-transitory computer-readable instructions that, when executed by one or more processors, configure the one or more processors to perform operations comprising:
receiving one or more images from an image capture device of a medical treatment location;
applying a trained machine learning model to the one or more images to detect presence of a patient in the medical treatment location, the trained machine learning model being trained to establish a relationship between one or more features of images of the medical treatment location and patient presence;
estimating a location of a gurney in the one or more images based on an output of the trained machine learning model;
applying one or more object recognition techniques to a portion of the one or more images corresponding to the location of the gurney to determine existence of the patient on the gurney including determining whether the patient exists or fails to exist on the gurney;
storing data indicating presence of the patient in the medical treatment location based on determining whether the patient exists or fails to exist on the gurney;
generating context assessment for the medical treatment location based on the stored data indicating presence of the patient; and transmitting, over a network, the context assessment for presentation on a user interface of a client device.

* * * * *